United States Patent
Grunkin et al.

(10) Patent No.: US 10,209,165 B2
(45) Date of Patent: Feb. 19, 2019

(54) ASSESSMENT OF STAINING QUALITY

(71) Applicant: Visiopharm A/S, Horsholm (DK)

(72) Inventors: Michael Grunkin, Skodsborg (DK); Johan Doré Hansen, Nærum (DK)

(73) Assignee: Visiopharm A/S, Horsholm (DK)

( * ) Notice: Subject to any disclaimer, the term of this patent is extended or adjusted under 35 U.S.C. 154(b) by 0 days.

(21) Appl. No.: 15/124,297

(22) PCT Filed: Mar. 9, 2015

(86) PCT No.: PCT/DK2015/050049
§ 371 (c)(1),
(2) Date: Sep. 7, 2016

(87) PCT Pub. No.: WO2015/135550
PCT Pub. Date: Sep. 17, 2015

(65) Prior Publication Data
US 2017/0212018 A1    Jul. 27, 2017

(30) Foreign Application Priority Data

Mar. 10, 2014  (DK) ................................. 2014 70115

(51) Int. Cl.
| | | |
|---|---|---|
| G01N 1/30 | (2006.01) | |
| G06K 9/00 | (2006.01) | |
| G06K 9/03 | (2006.01) | |
| G06T 7/00 | (2017.01) | |
| G16H 10/40 | (2018.01) | |

(52) U.S. Cl.
CPC .............. *G01N 1/30* (2013.01); *G06K 9/0014* (2013.01); *G06K 9/036* (2013.01); *G06T 7/0014* (2013.01); *G06T 2207/30024* (2013.01); *G06T 2207/30096* (2013.01); *G16H 10/40* (2018.01)

(58) Field of Classification Search
CPC ...................................................... G01N 1/30
See application file for complete search history.

(56) References Cited

U.S. PATENT DOCUMENTS

2008/0273788 A1    11/2008  Soenksen et al.

FOREIGN PATENT DOCUMENTS

| WO | WO-2009/020972 A2 | 2/2009 |
|---|---|---|
| WO | WO-2010/017822 A1 | 2/2010 |
| WO | WO-2010/033508 A1 | 3/2010 |

OTHER PUBLICATIONS

Wludarski et al. Appl Innunohistochem Mol Morphol., 2011, 19(2):112-118.*
Brügmann, et.al., Digital image analysis of membrane connectivity is a robust measure of HER2 immunostains; *Breast Cancer Res Treat*, 132: 41-49, 2011.
Dobson, et.al., Image analysis as an adjunct to manual HER-2 immunohistochemical review, *Histopathology*, 57: 27-38, 2012.
Laurinaviciene, et.al., Membrane connectivity estimated by digital image analysis of HER2 immunohistochemistry is concordant with visual scoring and fluorescence in situ hybridization results, *Diagnostic Pathology*, 6:87, 2011.
Wolff, et.al., American society of Clinical Oncology/College of American Pathologists Guideline Recommendations for Human Epidermal Growth Factor Receptor 2 Testing in Breast Cancer, *Journal of Clinical Oncology*, 25(1): 118-145, 2007.
Wolff, et.al., Recommendations for Human Epidermal Growth Factor Receptor 2 Testing in Breast Cancer, *Journal of Clinical Oncology*, 31(31): 3997-4013, 2013.

* cited by examiner

*Primary Examiner* — Bin Shen
(74) *Attorney, Agent, or Firm* — Dinsmore & Shohl LLP (57) ABSTRACT

The quality of staining histological specimens has an impact on the histological assessment of the specimen. One of the causes for variability in the accuracy is the variations in the staining of the specimens to be tested in the working laboratories. The present invention provides a method for assessing the staining quality in a working laboratory and providing a quantitative quality measure for the staining quality. Thereby, it is possible for each working laboratory to evaluate their staining quality and to get feedback of how to improve the quality. The invention further relates to a system and a software program for carrying out the method.

26 Claims, 7 Drawing Sheets

0/1+
Very small and disconnected
membrane objects

2+
Small mixed with larger
connected membrane objects

3+
Dominated by large connected
membrane objects

ASSESSMENT OF STAINING QUALITY

CROSS-REFERENCE TO RELATED APPLICATIONS

This application is the U.S. national stage of PCT/DK2015/050049 filed Mar. 9, 2015, which claims priority of Danish patent application PA 2014 70115 filed Mar. 10, 2014. The entire content of each application is incorporated herin by reference.

FIELD OF INVENTION

The present invention relates to methods for assessing the quality of tissue staining in a working laboratory.

BACKGROUND OF INVENTION

When performing histological assessments of specimens containing cells it is relevant to consider the quality of the staining before considering the histological findings in the specimen. Too little or too much staining as compared to a protocol may lead to incorrect evaluations of the specimen. In particularly if the specimen relates to tumor cells it may be crucial for the patient that the laboratory is capable of staining and evaluating the specimens correctly.

The human epidermal growth factor, commonly referred to as HER2, is amplified in approximately 18% to 20% of breast cancers. HER2 overexpression is associated with clinical outcomes in patients with breast cancer. Several studies have shown that agents that target HER2 are remarkably effective in both the metastatic and adjuvant settings. Trastuzumab (Herceptin; Genentech, South San Francisco, Calif.), a humanized monoclonal antibody, improves response rates, time to progression, and even survival when used alone or added to chemotherapy in metastatic breast cancer. Trastuzumab is also active as a single agent and was approved in 1998 by the US Food and Drug Administration for the treatment of metastatic disease.

The ASCO/CAP panel have issued guideline recommendations for HER2 testing in breast cancer, and it is recommended that HER2 status should be determined for all invasive (early stage or recurrence) breast cancer on the basis of one or more Her2 test results [1]. These guideline recommendations are adopted to a varying degree by different local national boards across the world.

In daily practice between 80 and 90 percent of primary HER2 testing in fx the United States is done with immunohistochemistry (IHC), while only 10 to 20 percent is done with FISH. Approximately 10 to 20 percent of IHC test results fall into the so-called "indeterminate" range, and those specimens are re-tested using FISH which is widely considered the Gold Standard. One reason for this practice is also price, where an IHC assay may cost $100 to $150, and a FISH assay may be double or triple that price The ASCO/CAP guidelines were recently updated in November 2013 [2]. The Update Committee was concerned about false-negative and false-positive HER2 assessments. For example, a false-negative test result could lead to denial of trastuzumab treatment for a patient who could benefit from it. False-positive results could lead to the administration of potentially toxic, costly, and ineffective adjuvant HER2-targeted therapy for 1 year.

The purpose of the ASCO/CAP guidelines is to improve the accuracy of human epidermal growth factor receptor 2 (HER2) testing in invasive breast cancer and its utility as a predictive marker.

Despite efforts to provide detailed guidelines for improving the accuracy of the testing of HER2 protein expression, numerous reports of variability in interpretation have raised uncertainty about the reliability of results.

SUMMARY OF INVENTION

The present inventors have found that one of the causes for variability in the accuracy is the variations in the staining of the specimens to be tested in the working laboratories. The present invention provides a method for assessing the staining quality in a working laboratory and providing a quantitative quality measure for the staining quality. Thereby, it is possible for each working laboratory to evaluate their staining quality and to get feedback of how to improve the quality.

Accordingly, the invention relates to a method for assessing the quality of staining of a specimen containing cells in a working laboratory comprising the steps of
   providing a plurality of said specimens containing cells,
   in said working laboratory staining at least one of said specimens according to a predetermined staining protocol thereby obtaining control specimen(s)
   providing a digital image of each of said control specimen(s),
   providing a digital image of at least one reference specimen, wherein said reference specimen(s) is one of said specimen containing cells having been stained according to said predetermined staining protocol and wherein said staining have been validated according to a standard,
   calculating at least one reference quality parameter value relating to the staining of the reference specimen(s) and at least one control quality parameter value relating to the staining of said control specimen(s),
   correlating the at least one reference quality parameter value with said at least one control quality parameter value, thereby obtaining a measure for the quality of staining of the specimen in the working laboratory.

All the steps of the method may be carried out at the working laboratory, or in a combination of the working laboratory and a standardized laboratory.

Additionally, the invention relates to a method for assessing the quality of tissue staining in a working laboratory comprising the steps of
   in a standardized laboratory
      providing a plurality of specimens
      staining at least one of said specimens according to a predetermined staining protocol thereby obtaining a reference specimen (s) and providing a digital image of each of said reference specimen(s),
      forwarding at least one specimen to the working laboratory to be stained according to said predetermined staining protocol in order to obtain control specimen(s),
      receiving from said working laboratory
         at least one control specimen and providing a digital image of each of said control specimen(s) or
         a digital image of each of said control specimen(s)
      calculating at least one reference quality parameter relating to the staining of the reference specimen(s) and at least one control quality parameter relating to the staining of said control specimen(s),
      correlating the at least one reference quality parameter with said at least one control quality parameter, thereby obtaining a measure for the quality of staining of the specimen in the working laboratory.

The invention further relates to a system and a software program for carrying out the method.

DEFINITIONS

Standardized laboratory means a laboratory providing reference specimens being stained in accordance with a predefined protocol and being validated, preferably validated through another method than the staining method in question.

Working laboratory means a laboratory carrying out histological examinations on cell containing specimens, said laboratory is to be assessed with respect to staining quality.

Reference specimen means a specimen stained at the standardized laboratory or stained according to a predetermined protocol and subsequently validated.

Control specimen means a specimen being stained according to a predetermined protocol at the working laboratory to be assessed.

Quality measure or quality score are used synonymously and means the quantitative measure for the quality of the staining in the working laboratory.

DETAILED DESCRIPTION OF THE INVENTION

The general principle of the method according to the invention lies in the comparison between the staining at the working laboratory with standardized staining achieved at a standardized laboratory, and determining a quantitative quality measure describing a quantitative relation between the staining at the working laboratory and the standardized staining, whereby it is possible to not only determine whether the staining is good or not, but also describing how bad the staining is, if it is not good.

The present invention relates to a method for assessing the quality of staining of specimens including cells. As discussed above, it is of importance that the staining quality is as high as possible to avoid misinterpretation of the findings in the specimens that may be ascribed to a lack of staining quality. In the following this is discussed in relation to breast cancer and staining for Her2, however the basic principle may be applied to any type of specimen containing cells.

Her2 Staining

The two fundamental ASCO/CAP evaluation criteria recommended for assessing HER2 protein expression are intensity and completeness: Intensity is described as Intense, Moderate, Weak, Faint, and Barely perceptible. Completeness are described as varying degrees between Complete and Incomplete.

The descriptive nature of these evaluation criteria are good at capturing key elements of the cognitive process of visual human assessment of a stained tissue specimen. It is clear, however, that the descriptive (although ordinal) nature of these criteria are open to considerable subjective interpretation which can only contribute to affect inter-lab and pathologist variability.

Moreover, the recommended application of the ASCO/CAP evaluation criteria stay silent on a number of issues that are important in a quantitative and standardization context:

1. There is very little or no research on exactly how and how much the two evaluation criteria (intensity and completeness) contribute individually to a meaningful description of protein (over) expression and/or predict gene amplification.
2. Although it is known that staining sufficiency play a central role in the assessment of HER2 protein expression, little is known about how much a given staining can be allowed to deviate from optimal staining parameters and how that affect results for manual reading as well as image analysis
3. Staining intensity is notorious for its variability as a function of tissue processing including stainer platform and reagent. Also, the specific digital imaging device and viewing device play an important role in how color and staining intensity is perceived and quantified. There are no well-defined and widely agreed standards for handling and controlling this type of variability.
4. Completeness is not easily defined except in the extreme cases with no positive staining at all, or where all tumor cells have intense and complete staining as in the typical chicken-wire pattern seen in clear-cut HER2 3+ cases. But for 1+ and 230 cases, it can be hard to tell whether a positive membrane between two neighboring tumor cells belong to one or the other. Or both. This makes it challenging to determine degrees of completeness, which is also not subject to well-defined standards.
5. Due to the 3-D structure of the tissue, we often see positive membranes in a section without its associated nucleus. Although these membranes contribute to our visual interpretation it is not obvious how such membrane objects should be handled in a quantitative context.

Different commercially available HER2 algorithms with regulatory clearance are available, and most of the methods reviewed in Dobson et al. [3] are based on quantification of intensity alone, and performance are measured as concordance with manual review.

Methods based on intensity alone will be vulnerable to contributions from cytoplasmic staining, as well as the general issues with variability in staining intensity. None of the intensity based methods are characterized in terms of sensitivity and specificity with respect to gene amplification measured with e.g. HER2-FISH.

Accordingly, it is of utmost importance that working laboratories perform the staining of the various specimens in accordance with standardized protocols, and the present invention provides a simple yet very effective way of providing a quantitative quality means which may be used by the involved working laboratories to correct their procedures in case their staining deviates too much from the reference specimens.

The method includes that at least two specimens of the same type are stained at the standardized laboratory and the working laboratory, respectively. The staining at the standardized laboratory is optimal according to the standardized protocol and the results are confirmed through another type of analysis, for example for breast cancer the other type of analysis may be a FISH test.

It has been found that it is possible to evaluate the quality of staining by comparing the stained reference specimen and control specimen and obtaining a quantitative measurement for the difference between the two staining procedures, see below for a method for quantitatively measuring the difference.

Specimens

The specimen may be any suitable specimen containing biological cells. Mostly the specimen is either a section of a tissue portion or a sample of fluid containing cells.

The tissue portion may come from any relevant tissue, and will typically come from tumor tissue or tissue suspected to contain tumor tissue. It may be any tumor, such as typically tumor tissue selected from breast tumor tissue, colon tumor tissue, bladder tumor tissue, kidney tumor tissue, endometrial tumor tissue, lung tumor tissue, melanoma tissue, and prostate tumor.

The specimen may also be a sample of fluid containing cells. The fluid may be a body fluid, such as blood, urine, saliva or cerebrospinal fluid, or the fluid may come from a lavage, such as bronchoalveolar lavage. The fluid may be examined for any type of cells, such as cancer cells.

A reference specimen must be well characterised with respect to the relevant cells or tissue, such as with respect to the true content of the marker to be stained.

It is preferred that the method is carried out using at least two reference specimens and two control specimens, more preferably carried out using at least three reference specimens and at least three control specimens. When three different specimens are used it is preferred that at least one negative control and one positive control is included together with a specimen being stainable in between the two extremes.

In particularly, if tumor tissue may be divided into different classes with respect to malignancy, it is relevant to include tumor tissue from more than one class. Preferably, tumor tissue from all classes are included, whereby there is a stained specimen for each class.

It is preferred, in order to secure homogeneity and equal conditions between the reference specimen(s) and the control specimen(s) that they are embedded in a block, such as a paraffin block. They may be embedded in a block each or one or more specimens in the same block. For example, when more reference specimens and control specimens are used it is advantageous if all reference specimens are embedded in one block and the control specimens are embedded in another block, or alternatively that both the reference specimens and the control specimens are embedded in the same block.

Staining

The staining may be any staining used in laboratories for staining specimens containing cells, such as tissue sections or fluid specimens.

Typically the staining is a staining specific for a marker in said specimen, such as a marker for protein expression, for example a protein expression specific for a specific type of cells in the specimen. An example is a staining for a marker associated with the cell membrane. Another example is a staining for the cell nucleus.

Examples of markers are selected from the IHC-family, such as HER2, ER, PR, Ki67, PHH3, CK5, cytokeratines, and CD antigens. In table 1, examples of epitopes being useful markers are shown. Table 1 is from the website of NordicQC.

TABLE 1

| epitopes useful as markers |
|---|
| A |
| alpha-methylacyl-CoA racemase (AMACR)<br>alpha-smooth muscle actin (ASMA)<br>Anaplastic lymphoma kinase (ALK) |
| B |
| B-cell specific activator protein (BSAP, Pax5)<br>bcl-2 protein<br>bcl-6 protein |
| C |
| Calretinin (CR)<br>Cancer antigen 125 (CA125)<br>Carcinoembryonic antigen (CEA)<br>CD3<br>CD4<br>CD5<br>CD8<br>CD10<br>CD14<br>CD15<br>CD19<br>CD20<br>CD23<br>CD30<br>CD31<br>CD34<br>CD45<br>CD56<br>CD68<br>CD79a<br>CD99<br>CD117<br>CD138<br>CD163<br>Cdx-2<br>Chromogranin (CGA)<br>Cyclin D1 (CyD1)<br>Cytokeratins (CKs) |
| D |
| Desmin |
| E |
| E-cadherin<br>Epithelial cell-cell adhesion mol. (Ep-CAM)<br>Epithelial membrane antigen (EMA)<br>Estrogen receptor (ER) |
| F |
| Factor VIII related antigen (FVIII) |
| G |
| Gross cystic fluid protein-15<br>Glial fibrillary acidic protein (GFAP) |
| H |
| Hepatocyte antigen (Hepa)<br>HER-2<br>Human chorionic gonadotropin (HCG) |
| I |
| Immunoglobulins (Ig) |
| K |
| Ki-67 |
| M |
| Mammaglobin<br>Melan-A (MLA)<br>Melanosoma specific antigen<br>(MSA, HMB-45) |

TABLE 1-continued epitopes useful as markers

Mismatch repair (MMR) proteins
Multiple myeloma oncogene 1 (MUM1)
Myosin (SMH)

N

Napsin A (NapA)
Neurofilament protein (NFP)

O

OCT3/4

P p16$^{ink4a}$
p53
p63
Paired Paired box gene protein 2 (PAX2)
Paired Paired box gene protein 8 (PAX8)
Placental Alkaline Phosphatase (PLAP)
Podoplanin (Podop)
Progesterone receptor (PR)
Prostate-specific antigen (PSA)
Prostatic acid phosphatas (PAP)
Prostein

S

S-100 protein beta (S100)
Synaptophysin (SYP)

T

Terminal deoxynucleotidyl
transferase (TdT)
Thyroid transcription factor-1 (TTF1)

V

Vimentin (VIM)

W

Wilms tumour-1 protein (WT1)

Normally only one staining is used to stain a specific marker in the specimen, and accordingly, the staining protocol may specify a single staining.

However, for some purposes it is relevant to use to different stainings, for example in order to identify cells associated with other cells or specific tissue, or to identify different types of cells. For example a double staining may be a physical double staining, wherein two different stainings are performed on the same specimen, or it may be a virtual double staining as described below.

When using an image analysis system it is possible to perform a virtual double staining on serial tissue sections, ie wherein one tissue section is stained with one staining and a neighbouring tissue section is stained with another staining and then the analysis is made based on a registration of images of the two tissue sections whereby the full information of the double staining is obtained. Accordingly, the present invention is also useful when the staining protocol specifies more than one staining, such as a double staining.

The reference specimens are stained under controlled conditions preferably using validated optimal staining protocols, such as protocols from the commercial vendors Dako®, Ventana® and Leica®.

Quality Parameter

The quality parameter is a quantitative parameter derived from the image of the stained specimen, and is described herein in common for both the reference quality parameter and the control quality parameter.

The quality parameter is any suitable quantitative parameter relating to the staining, such as the connectivity, intensity of staining, mitose index, number of cells, number of positive and negative nuclei, Allred-score, H-Score, area of positive and negative nuclei, D-score, and Nottingham index.

All of the parameters are normally used to describe the findings in the specimen and are affected by the staining quality. In the following the parameter connectivity is described. Connectivity is a measure of generalized membrane completeness in an image. It is typically measured across a population of tumor cells in a region subjected to analysis. It is a purely morphological measure reflecting ensemble properties of all positive membranes above a defined detection threshold.

Connectivity is a parameter independent of the other parameter in that:

Connectivity does not relate to membrane intensity, except for the detection threshold that determines when a membrane is included in the calculations or not.

Connectivity does not attempt to relate individual cell nuclei in the image to specific membrane objects.

Connectivity is exclusively calculated based on the size distribution of membrane objects identified in the image.

This has profound implications on how Connectivity can be used in practice: It is not necessary to specifically exclude stromal cells from calculations, as the Connectivity is calculated exclusively from membrane objects expressing some level of positive staining. This makes it fast and simple to define areas for quantification of protein expression. It also solves the problem of determining the membrane completeness for individual nuclei, with the indeterminate problem of assigning a membrane to one or both of two neighbouring nuclei.

Figure 3:
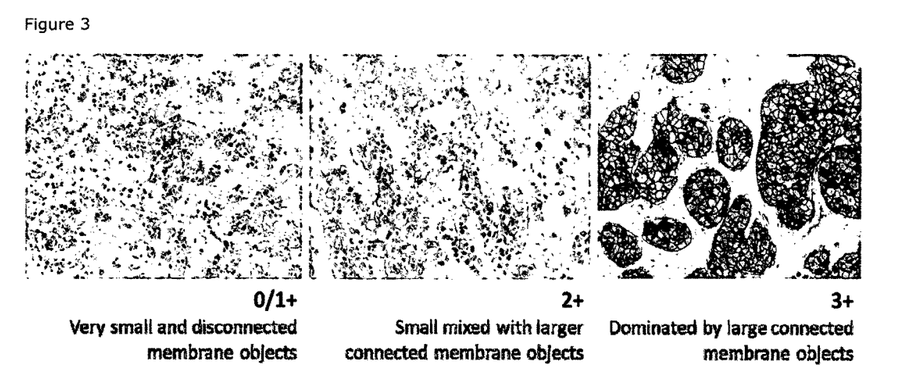
FIG. 3 shows specimens from 3 breast tumors being from 3 different classes.
Figure 4:
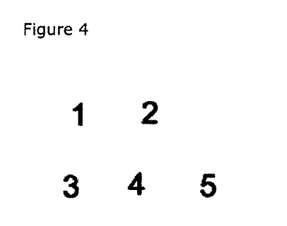
FIG. 4 shows 5 specimens embedded in one TMA block

In practical terms, connectivity is computed from the observed size (length) distribution of all positive membrane objects. In tumors with a low protein expressions, the membrane objects are few, isolated and small. In tumors with a high level the membrane objects are connected and large, as illustrated in FIG. 3.

As it is seen, the size distribution of membrane objects varies continuously between these two extremes. A few things should be noted about this principle:

Connectivity does not relate positive membrane objects to specific tumor cells, and does not include individual nuclei in the quantification. Only how positive membrane objects are related to each other in terms of connectedness.

Connectivity varies continuously between zero (0) and one (1). Minimum is achieved when there is no membrane, and Maximum when many neighboring tumor cells have complete membrane staining. Connectivity as a concept and as a method was introduced in 2011 [4,5].

Independent of the quality parameter selected, it may be defined as the mean, trimmed mean, median, or mode of the values determined for the quality parameter.

Reference Specimens

As discussed above, reference specimens are validated specimens. For example, they may be specimens stained according to the staining protocol in question and further validated. The validated procedure may either be manual, ie. where two or more experienced human graders evaluate the reference specimens before they are used as such. In another embodiment the reference specimens are validated through another separate analysis, for example through a FISH test.

Reference specimens may be produced at a standardized laboratory, or may be provided by other laboratories and then evaluated against the standard.

Figure 5A:
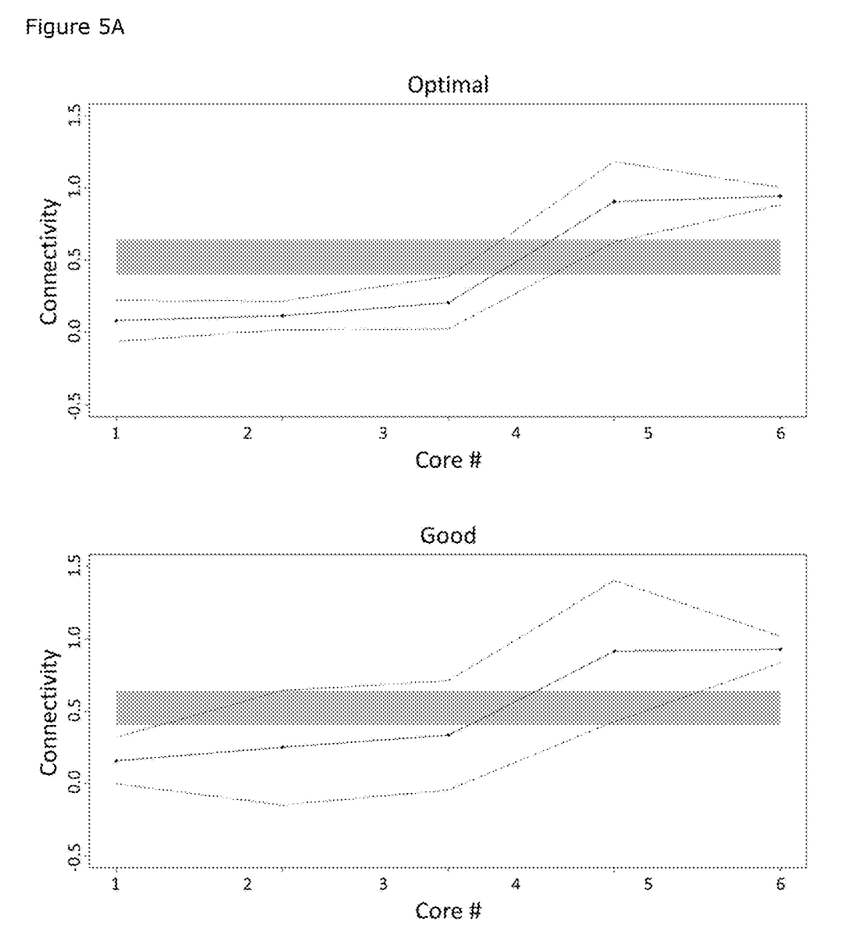
FIGS. 5A and 5B show the median level of connectivity plotted for each tumor specimen and versus gene expression levels. For each tumor specimen, empirical 95% confidence intervals are determined across all labs within a given quality category, and is shown as dotted lines.
Figure 5B:
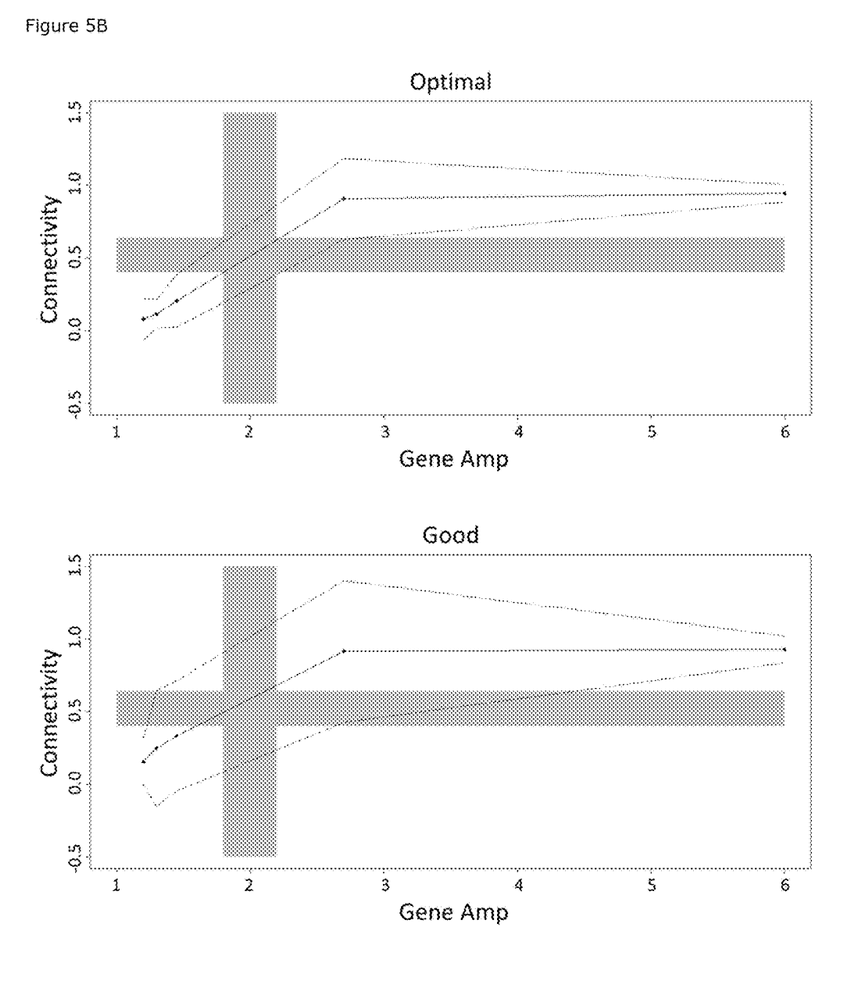
Figure 6:
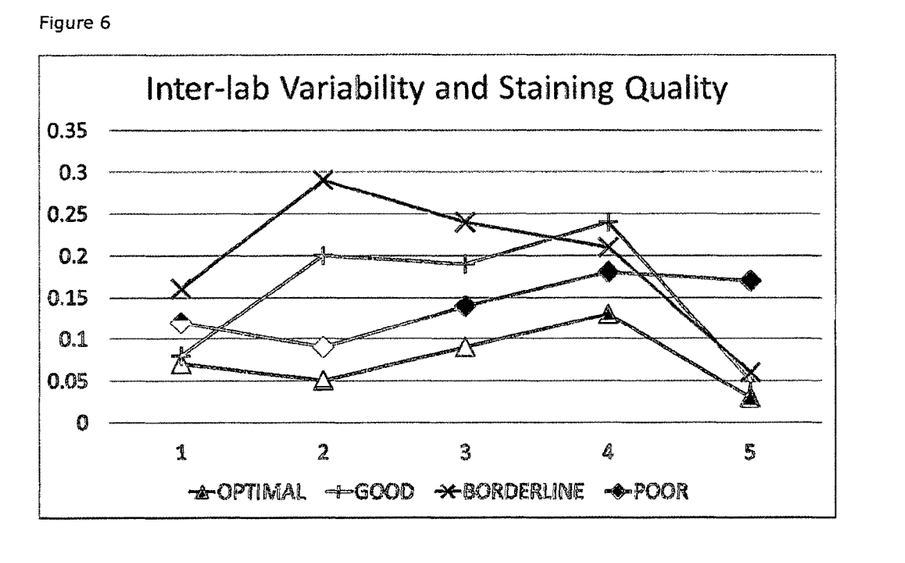
FIG. 6 shows the interlab variability and staining quality.

Typically, more than one reference specimen is provided, wherein the reference quality parameter value is calculated as the mean, trimmed mean, median, and/or mode value as discussed above, and the reference quality parameter value may then be presented with confidence intervals depicted, see for example FIGS. 5a and 5b.

Determination of a Measure of Quality of Staining

The measure of quality is determined from the quality parameters used. The same quality parameter is used for the reference specimens and the control specimens. For each quality parameter a value is calculated, and the quality measure is obtained from a correlation of the values from the reference specimens and the control specimens, respectively.

In one embodiment the quality measure is obtained as the difference between the reference quality parameter value(s) and the control quality parameter values(s), such as the numerical difference. The difference may be measured as the Euclidian distance, the maximum distance and/or the sum of absolute distances. Furthermore, the difference may be a weighted distance, for example a weighted distance taking into account the direction of the distance.

In another embodiment the quality measure is obtained as a ratio between the reference quality parameter value and the control quality parameter value.

The resulting quality measure may be presented as an absolute figure, or presented graphically as shown in the figures.

An example of using connectivity as the quality parameter and the related calculations is discussed further in the Examples below.

Image Analysis

Image analysis according to this invention may be performed according to any suitable image analysis system. Preferred examples are described in PCT/DK2007/050171 and PCT/D K2009/050202.

In a preferred embodiment each stained specimen is subjected to digital imaging, producing an image of each specimen. A vector of reference images is defined for each reference specimen:

$$\overline{S_I^R} = \begin{pmatrix} S_{i,1}^R \\ \vdots \\ S_{i,N_T}^R \end{pmatrix}, i = 1, \ldots, N_R$$

In other words, $S_{i,j}^R$ is a digital Reference Image of tumor j obtained from Reference section i Imaging may be performed using either a digital slide scanner or a microscope equipped with a digital camera.

In order to obtain a quantitative measure of staining quality (QS), it is preferred to have an image analysis method, providing a validated quantitative measure of the marker to be stained, such as a biomarker expression.

$IA(S, ROI)_{Marker}$, is an image analysis method that is providing a quantitative readout of biomarker expression on a given digital image, S, within a Region Of Interest (ROI). The ROI may be defined manually, or using an image analysis method.

Based on these definitions, it is possible to define a Reference Level, $L_i^R$, $i=1, \ldots, N_T$ for each of the reference specimens, which is defined as a Reference value or a reference Vector:

$$\overline{L^R} = \begin{pmatrix} L_1^R \\ \vdots \\ L_{N_T}^R \end{pmatrix}$$

The Reference Level is calculated from the Reference Images, using the Image Analysis Method. The purpose of the Reference Level is to define the "typical" level of marker for a given Reference specimen, sometimes referred to as the central tendency.

The Reference Level may be obtained as mean, trimmed mean, median, mode or other sample statistic that reflect the central tendency of a sampled set of Reference Images for a stained Reference Tumor.

The Reference Levels may for example be obtained as the mean value:

$$\overline{L^R} = \begin{pmatrix} L_1^R \\ \vdots \\ L_{N_T}^R \end{pmatrix} = \frac{1}{N_R} \sum_{i=1}^{N_R} \begin{pmatrix} IA(S_{i,1}^R, ROI_{1,i}) \\ \vdots \\ IA(S_{i,N_T}^R, ROI_{N_T,i}) \end{pmatrix}$$

Where $ROI_{j,i}$ is the Region Of Interest defined for Reference Tumor j on Reference Image i. The biomarker expression is calculated only within the ROI.

In practice, "outliers" may occur within the set of Reference Images. This may be due to various influences, including artifacts. In order to minimize the potential effect of outliers, it is always useful to consider robust estimators of central tendency. One approach is the so-called trimmed mean[1], where all the values are sorted. The α-trimmed mean is then obtained by eliminating the α/2 largest and smallest values. For α=50% we obtain the median. The median is the preferred estimator of central tendency.

[1] http://www.statistics.com/index.php?page=glossary&term_id=866

In a preferred embodiment, the staining quality for a specific lab is characterized as the ensemble deviation of all control sections from the respective reference levels, only.

Automated System and Software

In another aspect, the present invention further encompasses an automated or semi-automated system suitable for carrying out one or more of the methods disclosed herein, said automated or semi-automated system comprising, in combination:

a database capable of including a plurality of images of the specimens;

a software module for analyzing an image of the specimen;

a control module comprising instructions for carrying out said method(s).

Said automated or semi-automated system can also further comprise a scanner and a view screen, and/or a microscope and a camera.

Using a fully automated microscope, it is possible to let the system switch between low and high magnification. By using low magnification, it is possible to obtain a "super-lens" representation providing an overview of the entire slide, and let the system automatically identify regions on the slide containing tissue, using image analysis.

The system may further include a general processor and peripherals for printing, storage, etc. The general processor can be a microprocessor based microcomputer, although it may be another computer-type device suitable for efficient execution of the functions described herein. The general processor can for example control the functioning and the flow of data between components of the device, and handles the storage of representation and classification information. The general processor can additionally control peripheral devices such as a printer, a storage device, such as an optical or magnetic hard disk, a tape drive, etc., as well as other devices including a bar code reader, a slide marker, autofocus circuitry, a robotic slide handler, the stage, and a mouse.

Preferably, the images obtained are monochrome representations, color representations, or multi-frame (e.g. multispectral) images. Images are preferably stored as TIFF representations, or as JPEG or other standard formats.

In another embodiment the image may be acquired from a virtual slide obtained by means of a virtual microscope imaging the cell specimen in question. In this embodiment, the entire tissue area has been scanned at high magnification in e.g. a virtual slide scanner, and the resulting representation is already stored, for example on the harddisk. The system now handles this large representation as if it was controlling a microscope, stage, camera etc. Thus, the user can use the exact same interface to work with virtual microscope representations as when working with an actual microscope.

Computer Readable Medium or Software

In another aspect, the present invention further encompasses a computer readable medium or software program comprising instructions for carrying out one or more of the methods disclosed herein. Suitable computer-readable media can for example be a hard disk to provide storage of data, data structures, computer-executable instructions, and the like. Other types of media which are readable by a computer, such as removable magnetic disks, CDs, magnetic cassettes, flash memory cards, digital video disks, and the like, may also be used.

EXAMPLES

Quality Measures Determined for HER2-IHC Staining

This example uses the data and specimens obtained by NordiQC in their annual quality runs for HER2-IHC. Assessment run B12 for HER2-IHC, comprised a total of 5 tissues breast carcinoma tissue.

Figure 1:
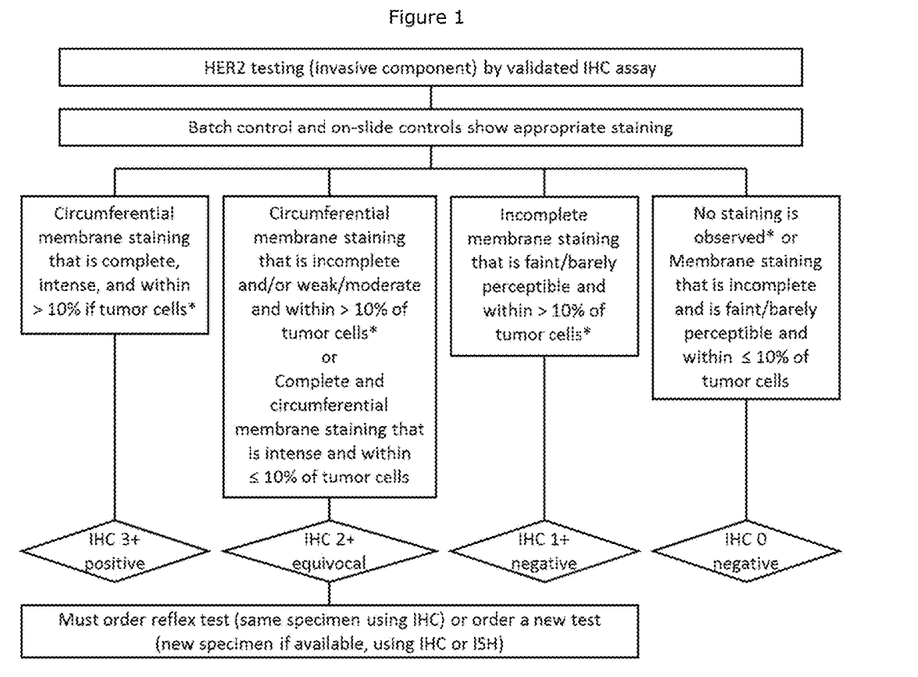
FIG. 1 shows the evaluation criteria for breast cancer specimens.
Figure 2:
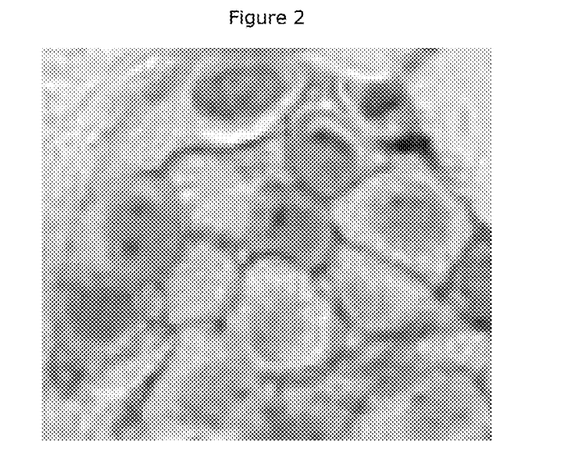
FIG. 2 shows a specimen from a breast cancer specimen being stained for Her2.

All carcinomas were fixed for 24-48 hours in 10% neutral buffered formalin, and embedded in a paraffin block as shown in FIG. 2. Control Sections were sent to participating labs for staining.

The Reference Tumors were well characterized as shown in the table below:

| | | IHC HER2 Score (0, 1+, 2+, 3+) | FISH HER2/Chr17 ration |
|---|---|---|---|
| 1. | BREAST DUCTAL CARCINOMA | 0 | 1.1-1.3 |
| 2 | BREAST DUCTAL CARCINOMA | 1+ | 1 2-1 4 |
| 3. | BREAST DUCTAL CARCINOMA | 1+/2+ | 1.3-1.6 |
| 4. | BREAST DUCTAL CARCINOMA | 2+ | 2.5-2.9 |
| 5. | BREAST DUCTAL CARCINOMA | 3+ | >6.0, Clusters |

A set of criteria for assessing quality of the HER2 staining were defined by the NordiQC as listed below:

| MANUAL QUALITY GRADE | |
|---|---|
| OPTIMAL | A clear and unequivocal staining marked as score 0 or 1+ in the breast ductal carcinomas no. 1 & 2. |
| | A clear and unequivocal staining marked as score 1+ or 2+ in the breast ductal carcinoma no 3. |
| | A clear and unequivocal staining marked as score 2+ or 3+ in the breast ductal carcinoma no 4. |
| | A clear and unequivocal staining marked as score 3+ in the breast ductal carcinoma no 5. |
| | No or only a weak cytoplasmic reaction that did not affect the interpretation of the true membranous HER-2 reaction. |
| GOOD | If the HER-2 gene amplified tumour no. 5 showed a 2+ reaction (an equivocal 2+ IHC staining should always be analyzed by ISH according to the ASCO/CAP guidelines and the national guidelines in Scandinavia) and the other breast carcinomas showed a reaction pattern as described above |
| BORDER-LINE | If the signal-to-noise ratio was low, e.g., because of moderate cytoplasmic reaction, excessive counterstaining or excessive retrieval hampering the interpretation |
| POOR | In case of a false negative staining (e.g. the 3+ tumour and the 2+ tumour with gene amplification showing a 0 or 1+ reaction) or a false positive staining (e.g. the 0, 1+ and 2+ tumours without gene amplification showing a 3+ reaction). |

A total of 232 laboratories participated in the assessment. Stainings from 153 participating laboratories (~65%) were assessed as Optimal, 23 as Good, 7 as Borderline, and 45 as Poor. For a total of four (4) labs, no slides and/or assessment was available.

Stained Control specimens from each of the participating labs, were scanned using a Hamamatsu Nanozoomer HT at 20× magnification, producing a digital Control Image of each tissue from each lab. Each Control Image was analyzed using the HER2-CONNECT algorithm (Visiopharm A/S, Denmark) in a Region Of Interest (ROI), resulting in a connectivity value for each control image.

The median connectivity was calculated for all Control Images receiving the grade Optimal by the NordiQC assessor panel.

| Ref. tumor | Gene amp | Median | Score |
|---|---|---|---|
| 1 | 1.2 | 0.08 | 0/1+ |
| 2 | 1.3 | 0.12 | 0/1+ |
| 3 | 1.45 | 0.21 | 0/1+ |
| 4 | 2.7 | 0.9 | 3+ |
| 5 | 6 | 0.94 | 3+ |

In the table below, the Median connectivity is estimated for each tumor across participating pathology labs given the same quality score by the NordiQC assessor panel. Also the inter-lab variability is determined, and expressed as the standard deviation across labs.

| Ref. tumor | Gene amp | Optimal | | | Good | | | Borderline | | | Poor | | |
|---|---|---|---|---|---|---|---|---|---|---|---|---|---|
| | | Median | Sdev | Score | Median | Sdev | Score | Median | Sdev | Score | Median | Sdev | Score |
| 1 | 1.2 | 0.08 | 0.07 | TN | 0.15 | 0.08 | TN | 0.24 | 0.16 | TN | 0.07 | 0.12 | TN |
| 2 | 1.3 | 0.12 | 0.05 | TN | 0.3 | 0.2 | TN | 0.66 | 0.29 | FP | 0.08 | 0.09 | TN |
| 3 | 1.45 | 0.21 | 0.09 | TN | 0.37 | 0.19 | TN | 0.46 | 0.24 | 2+ | 0.13 | 0.14 | TN |
| 4 | 2.7 | 0.9 | 0.14 | TP | 0.79 | 0.24 | TP | 0.95 | 0.21 | TP | 0.23 | 0.18 | FN |
| 5 | 6 | 0.94 | 0.03 | TP | 0.92 | 0.05 | TP | 0.91 | 0.06 | TP | 0.87 | 0.17 | TP |

In FIGS. 5a and 5b, the median level of Connectivity is plotted for each tumor specimen and versus gene expression levels respectively. For each tumor specimen, empirical 95% confidence intervals are determined across all labs within a given quality category, and shown as dotted lines.

The grey horizontal band in the two plots correspond to connectivity values in the interval ]0.40; 0.64], that are corresponding to equivocal readings, or 2+. Connectivity values below this interval are all HER2 negative, whereas Connectivity values above are HER2 positive.

The vertical grey band in FIG. 5b correspond to gene amplification values in the interval [1.8; 2.2] that, according to the ASCO/CAP guidelines are equivocal or 2+.

The following observations are made:
  Both Optimal and Good staining category allow for correct classification of tumors as HER2 positive and negative respectively.
  The Borderline Category has a tendency to give False Positive readings. The Poor category gives False Negative readings.
  Deviation from optimal staining quality does not only affect the ability to quantify the protein expression level correctly. Lack of staining sufficiency also has significant impact on the inter-lab variability.

Observations:
  For pathology labs with optimal staining, the inter lab variation is in the 3% -14% range, across different stainer-platforms. This is comparable to gene expression assays.
  As soon as the staining quality is below optimal, the inter-lab variability across cores increases with a factor of 4-6 across cores.
  For pathology labs with a Poor staining quality the variability is lower than for Good and Borderline, but with a problematic lack of sensitivity.

The Quality measure for a given pathology lab (and marker) is calculated from digital images of Control specimens stained at the lab. Connectivity is calculated for each of the Control Images, $C_i$, i=1, . . . , 5 and compared to the Reference Levels, $L_i^R$, i=1, . . . , 5 calculated as described above. Here, the Euclidian distance between Connectivity is calculated for the Control Images and the corresponding Reference images:

$$QS = \sqrt{(C_1 - 0.08)^2 + (C_2 - 0.12)^2 + (C_3 - 0.21)^2 + (C_4 - 0.9)^2 + (C_5 - 0.94)^2}$$

Figure 7:
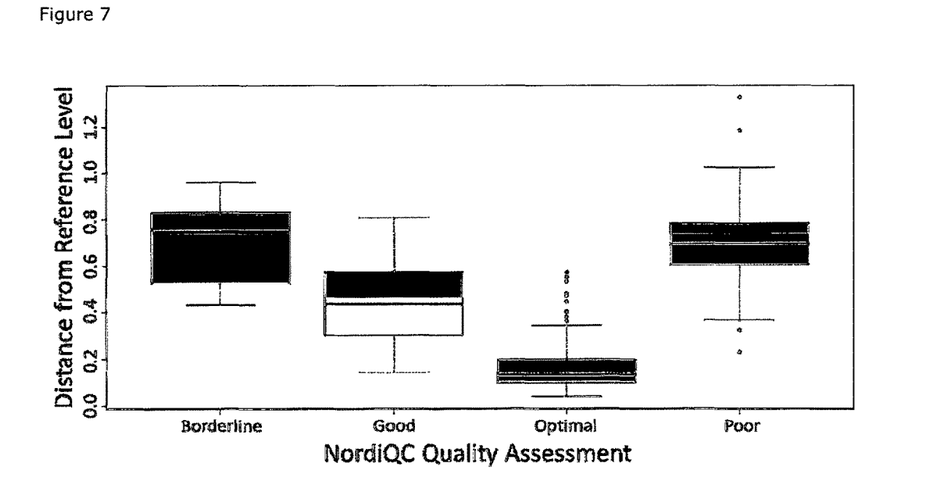
FIG. 7 shows the quality measure calculated for control specimens from 228 laboratories. The Box-Whisker plot shows values plotted against the manual Quality Score assigned by an assessor panel from the independent scientific organization NordiQC.

The Quality measure is calculated for the control specimens from all 228 labs. In the Box-Whisker plot below, values are plotted against the manual Quality measure assigned by the NordiQC assessor panel.

REFERENCES

1. Wolff et al, 2013; Recommendations for Human Epidermal Growth Factor Receptor 2 Testing in Breast Cancer: American Society of Clinical Oncology/College of American Pathologists Clinical Practice Guideline Update; Journal of Clinical Oncology; Vol 31, Number 31
2. Wolff et al, 2007; American Society of Clinical Oncology/College of American Pathologists Guideline Recommendations for Human Epidermal Growth Factor Receptor 2 Testing in Breast Cancer; Arch Pathol Lad Med; Vol 131
3. Dobson et al, 2012; Image analysis as an adjunct to manual HER-2 immunohistochemical review: a diagnostic tool to standardize interpretation; Histopathology, 57, 27-38
4. Brügmann et al, 2011; Digital image analysis of membrane connectivity is a robust measure of HER2 immunostains; Breast Cancer Res Treat
5. Laurinaviciene et al, 2011; Membrane connectivity estimated by digital image analysis of HER2 immunohistochemistry is concordant with visual scoring and fluorescence in situ hybridization results: algorithm evaluation on breast cancer tissue microarrays; Diagnostic Pathology

The invention claimed is:
1. An automated or semi-automated method for assessing the quality of staining of a specimen containing cells in a standardized laboratory using a digital image analysis system comprising a computer processor, the staining being a staining specific for a marker in the specimen, the method comprising the steps of:
  a) providing a plurality of specimens of the same type, the specimens containing cells;
  b) staining the marker in at least one of the specimens according to a predetermined staining protocol by the standardized laboratory thereby obtaining a reference specimen(s);
  c) digitally imaging each of the reference specimen(s);
  d) forwarding at least an unstained one of the specimens to a working laboratory to be stained according to the predetermined staining protocol in order to obtain a control specimen(s);
  e) digitally imaging each of the control specimen(s) and receiving at the standardized laboratory from the working laboratory the digital image of each of the control specimen(s) or receiving at the standardized laboratory from the working laboratory the control specimen(s) and digitally imaging each of the control specimen(s);
  f) deriving by the digital image analysis system for each of the reference specimen(s) from the image of each reference specimen a quality parameter relating to the staining, wherein the quality parameter is selected from the group consisting of connectivity, mitose index, number of cells, number of positive and negative nuclei, Allred-score, H-Score, area of positive and negative nuclei, D-score, and Nottingham index using an image analysis method that provides a quantitative readout of the marker on a given digital image;
  g) calculating a reference level as a mean, trimmed mean, median or mode of the quality parameter(s) of all of the reference specimen(s), the reference level representing a central tendency of the marker for a given reference specimen;

h) deriving by the digital image analysis system for one of the control specimen(s) the quality parameter from the image of the control specimen using the image analysis method; and i) obtaining a deviation of the quality parameter of the control specimen by comparing the quality parameter of the control specimen to be assessed with the reference level, wherein the deviation of the quality parameter can be used as a quantitative measure for the quality of staining of the control specimen in the working laboratory to correct their staining procedure thereby improving their staining quality.

2. The method according to claim 1, wherein the at least three reference specimens and at least three control specimens are provided.

3. The method according to claim 1, wherein at least one negative control and at least one positive control is included among the specimens.

4. The method according claim 1, wherein the reference specimen(s) is(are) embedded in one block, and the control specimen(s) is(are) embedded in one other block.

5. The method according to claim 1, wherein the specimen is a section of a tissue portion or a sample of fluid comprising cells.

6. The method according to claim 5, wherein the tissue is tumor tissue selected from breast tumor tissue, colon tumor tissue, bladder tumor tissue, kidney tumor tissue, endometrial tumor tissue, lung tumor tissue, melanoma tissue, or prostate tumor.

7. The method according to claim 6, wherein the tumor tissue is classifiable into at least two classes, and wherein there is stained a specimen for each class.

8. The method according to claim 7, wherein the quality parameter is calculated as a total for all classes.

9. The method according to claim 7, wherein one quality parameter is calculated for each class.

10. The method according to claim 5, wherein the sample of fluid is a body fluid sample.

11. The method according to claim 1, wherein the marker is a marker for protein expression.

12. The method according to claim 11, wherein the marker is associated with the cell membrane or the marker is associated with the cell nucleus.

13. The method according to claim 12, wherein the marker is selected from the IHC-family, including at least HER2, ER, PR, Ki67, PHH3, CK5, cytokeratines, and CD antigens.

14. The method according to claim 1, wherein the staining protocol specifies a single staining.

15. The method according to claim 1, wherein the staining protocol specifies a physical double staining.

16. The method according to claim 1, wherein control or reference slides containing the control or reference specimen(s) are accompanied by a second slide containing a serial section of said specimen.

17. The method according to claim 16, where said serial section is used for virtual double staining.

18. The method according to claim 1, wherein the deviation is a numerical difference.

19. The method according to claim 18, wherein the numerical difference is measured as the Euclidian distance, the maximum distance or sum of absolute distances.

20. The method according to claim 18, wherein the numerical difference is a weighted distance, wherein the weighted distance taking into account the direction of the distance.

21. The method according to claim 1, wherein the deviation is a ratio between the quality parameter of the reference specimen(s) and the quality parameter of the control specimen(s).

22. The method according to claim 1, wherein the resulting measure for quality is presented as a figure or a graph.

23. The automated or semi-automated method according to claim 1, wherein the assessment is performed by an independent organization.

24. An automated or semi-automated method for assessing the quality of staining of a specimen containing cells in a working laboratory using a digital image analysis system comprising a computer processor, the staining being a staining specific for a marker in the specimen, the method comprising the steps of:

a) providing a plurality of specimens of the same type, said specimens containing cells;

b) staining the marker in each of the plurality of said specimens in one of participating working labs according to a predetermined staining protocol thereby obtaining control specimens;

c) digitally imaging each stained specimen;

d) validating staining of the plurality of said specimen by:
assessing quality of the staining and assigning each of the assessed specimen a grade; and
selecting the assessed control specimens receiving a grade higher than a certain grade as reference specimens;

e) deriving by the digital image analysis system for each of the reference specimens from the image of each reference specimen a quality parameter relating to the staining, wherein the quality parameter is selected from the group consisting of connectivity, mitose index, number of cells, number of positive and negative nuclei, Allred-score, H-Score, area of positive and negative nuclei, D-score, and Nottingham index using an image analysis method that provides a quantitative readout of the marker on a given digital image;

f) calculating a reference level as a mean, trimmed mean, median or mode of the quality parameters of all the reference specimens, the reference level representing a central tendency of the marker for a given reference specimen;

g) deriving by the digital image analysis system for one of the control specimens the quality parameter from the image of the control specimen using the image analysis method; and h) obtaining a deviation of the quality parameter of the control specimen by comparing the quality parameter of the control specimen to be assessed with the reference level, wherein the deviation of the quality parameter can be used as a quantitative measure for the quality of staining of the control specimen in the working laboratory to correct their staining procedure thereby improving their staining quality.

25. The method according to claim 24, wherein the grade includes optimal, good, borderline or poor.

26. The method according to claim 24, wherein there are multiple types of the specimens and there is a reference level for each type.

* * * * *